(12) United States Patent
Wang et al.

(10) Patent No.: US 8,397,791 B2
(45) Date of Patent: Mar. 19, 2013

(54) ZIRCONIUM OXIDE DENTAL IMPLANT WITH INTERNAL THREAD AND POLYGONAL TAPERING SECTION, AND THE MOLD FOR MOLDING THE SAME

(75) Inventors: Min-Wen Wang, Kaohsiung (TW); Chia-Wei Yu, Hsinchu County (TW)

(73) Assignee: National Kaohsiung University of Applied Sciences, Kaohsiung (TW)

( * ) Notice: Subject to any disclaimer, the term of this patent is extended or adjusted under 35 U.S.C. 154(b) by 0 days.

(21) Appl. No.: 13/116,496

(22) Filed: May 26, 2011

(65) Prior Publication Data

US 2012/0301849 A1    Nov. 29, 2012

(51) Int. Cl.
*B22D 17/00* (2006.01)
*B29C 45/00* (2006.01)
*B29D 1/00* (2006.01)

(52) U.S. Cl. ............. 164/312; 425/577; 249/59

(58) Field of Classification Search .......... 164/306–318; 425/418, 556, 577, 438; 249/59
See application file for complete search history.

(56) References Cited

U.S. PATENT DOCUMENTS

| | | | | |
|---|---|---|---|---|
| 4,842,462 A | * | 6/1989 | Tildesley | 411/180 |
| 6,280,193 B1 | * | 8/2001 | Peltier | 433/174 |
| 2008/0286721 A1 | * | 11/2008 | Walther | 433/174 |

* cited by examiner

*Primary Examiner* — Kuang Lin
(74) *Attorney, Agent, or Firm* — Muncy, Geissler, Olds & Lowe, PLLC (57) ABSTRACT

A mold for molding a green body for manufacturing a zirconium oxide dental implant includes a first molding part and a second molding part. The first and second molding parts each has a first imprinting inner surface and two none-thread inner surfaces for forming the external of the green body with two external thread sections and two none-thread sections. The mold may also include a driving mechanism, a polygonal conical slider and a screw thread forming rod. The polygonal conical slider can be driven for axially sliding into the mold cavity without rotation. The screw thread forming rod is coaxially and slidably penetrated the polygonal conical slider and driven by the driving mechanism for screwing into the mold cavity and unscrewing out of the mold cavity thereby forming the inner of the green body with an internal thread and a polygonal tapering section.

4 Claims, 10 Drawing Sheets

ZIRCONIUM OXIDE DENTAL IMPLANT WITH INTERNAL THREAD AND POLYGONAL TAPERING SECTION, AND THE MOLD FOR MOLDING THE SAME

BACKGROUND OF THE INVENTION

1. Field of the Invention

The present invention relates generally to a zirconium oxide dental implant manufactured by molding a green body and sintering the green body, especially to a mold for molding the green body for sintering to be a zirconium oxide dental implant with at least an external thread, internal thread and polygonal tapering section.

2. Description of the Related Art

Figure 1:
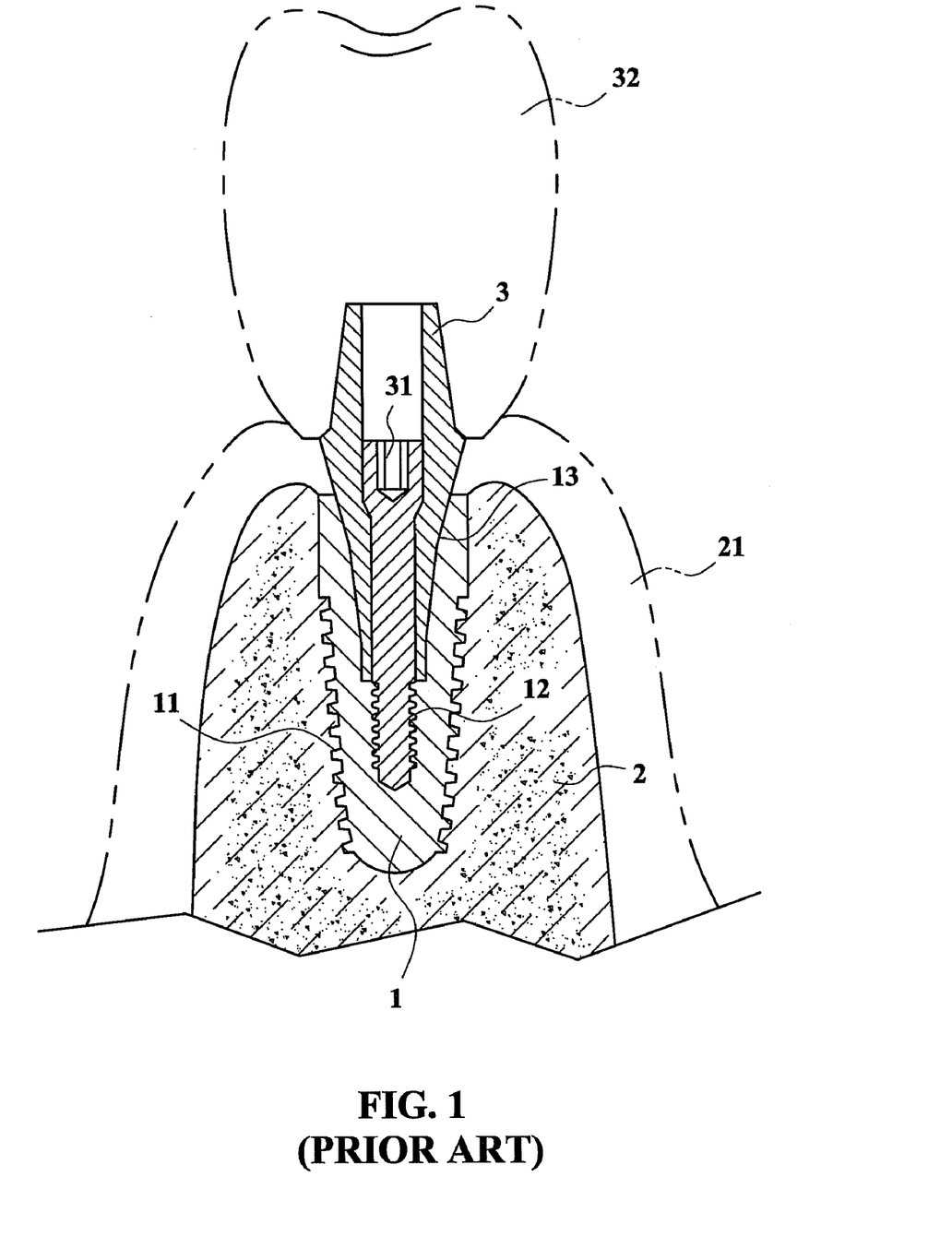
FIG. 1 is a cross-sectional schematic view illustrating a typical use of an ordinary dental implant connecting a dental crown cap to an alveolar bone through an abutment and securing screw.

As being illustrated in FIG. 1, the typical use of ordinary dental implant 1 is for connecting a dental crown cap 32 to alveolar bone 2 through an abutment 3. Some products of the dental implant 1 may be formed with an internal thread 12 for securing the abutment 3 by securing screw 31.

The majority of the implants valuable for osseous tissues are made of titanium as pure as possible. These titanium implants 1 are generally tightly fitted in a drill hole at the alveolar bone 2, each formed with an external thread 11 on the peripheral so as to be screwed into the alveolar bone 2, this gives a better security in the quality of the fixing.

Since a few years, new implants are under experimentation. Some of them have been adopted successfully like those made of zirconium oxide with a particularly good robustness linked to the hardness of the zirconium oxide material and consequently a longer life.

Zirconium oxide implants available today may have sometimes a central axial conical hole, the shape of which is polygonal, more often square or hexagonal. Their hole is obtained by molding and then sintering and they can receive prosthetics with a similar shape which have to be adjusted in the well before fixing with dental cement.

However, even with these techniques, the longevity of these zirconium oxide implants is not optimal. In fact, due to the extreme hardness of the material, it is not possible to drill correctly this threaded hole once the implant has been molded. A better solution has provided by U.S. Pat. No. 5,846,136 as being illustrated in FIG. 2, in which a green body 10 can be manufactured by an insert holding mechanism 7, a first molding part 71, a second molding part 72, and a plurality of metal inserts 7c, 7d. The external thread 11 of the green body 10 is formed in a mold cavity between the molding parts 71, 72. An internal thread 12 and a polygonal tapering section are formed by the metal inserts 7c, 7d both of which have to be unscrewed by specific tools from the green body 10 after molded. The metal insert 7c has a rounded shoulder for detachably engaging with a metal ball 7a biased by a spring 7b, and this can be discharged by pulling downward from the insert holding mechanism 7, when the green body 10 is molded in the mold cavity.

Figure 2:
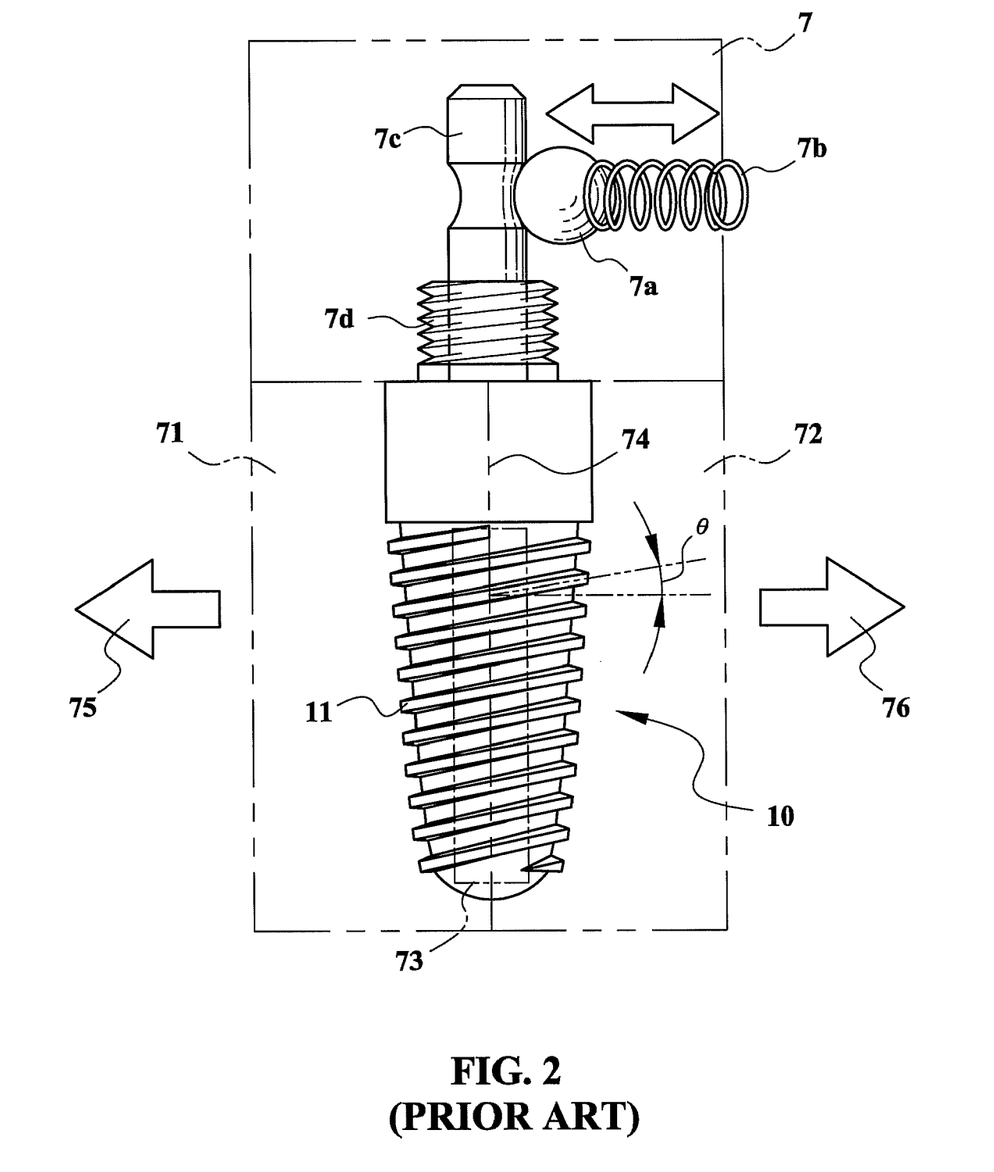
FIG. 2 is a cross-sectional schematic view illustrating a patented mold of a related art that can use to mold a green body together with some metal inserts; the green body can be sintered to be a zirconium oxide dental implant after the metal inserts being unscrewed from the green body.

Since the direction of the external thread 11 has a thread angle θ and not be possible parallel to the opening direction 75, 76 of the molding part 71, 72, the opening of the mold cavity shall unavoidably and slightly tear off and distort the external thread 11 at the area 73 near the parting line 74. Due to the green body 10 is highly breakable before sintered in high temperature, the operation of unscrewing the metal inserts 7c, 7d and the opening of the mold cavity may cause the green body 10 broken or fracture from time to time in mass production.

SUMMARY OF THE INVENTION

For simplifying the mold of manufacturing the green body of zirconium oxide dental implant and eliminating the troublesome of removing the metal inserts, the present invention provides a zirconium oxide dental implant which can be manufactured by injecting a zirconium oxide paste in a mold for obtaining a green body and sintering the green body to be the zirconium oxide dental implant. The green body is formed integrally with a first external thread section, a first none-thread section, a second external thread section, second none-thread section, wherein the first external thread section and the second external thread section are formed on the peripheral of the green body and divided by the first none-thread section and the second none-thread section.

The mold may include at least a first molding part and a second molding part. The first molding part has a first imprinting inner surface for forming the first external thread section of the green body, and two none-thread inner surfaces for forming a half portion of the first none-thread section and the second none-thread section of the green body respectively.

The second molding part has a second imprinting inner surface for forming the second external thread section of the green body, and two none-thread inner surfaces for forming a half portion of the first none-thread section and the second none-thread section of the green body respectively.

Preferably, the mold may further include a driving mechanism, a polygonal conical slider and a screw thread forming rod for forming a internal thread and a polygonal tapering section in the green body. The polygonal conical slider is driven by the driving mechanism 44 for axially sliding into the mold cavity without performing rotation.

The screw thread forming rod is coaxially and slidably penetrated the polygonal conical slider and driven by the driving mechanism for screwing into the mold cavity and unscrewing out of the mold cavity.

BRIEF DESCRIPTION OF THE DRAWINGS

The accompanying drawings, which are included to provide a further understanding of the invention are incorporated in and constitute a part of this specification, illustrate embodiments of the invention and together with the description serve to explain the principles of the invention. In the drawings.

DETAILED DESCRIPTION OF THE PREFERRED EMBODIMENTS

Reference will now be made in detail to the preferred embodiments of the present invention; examples of which are illustrated in the accompanying drawings.

Figure 6:
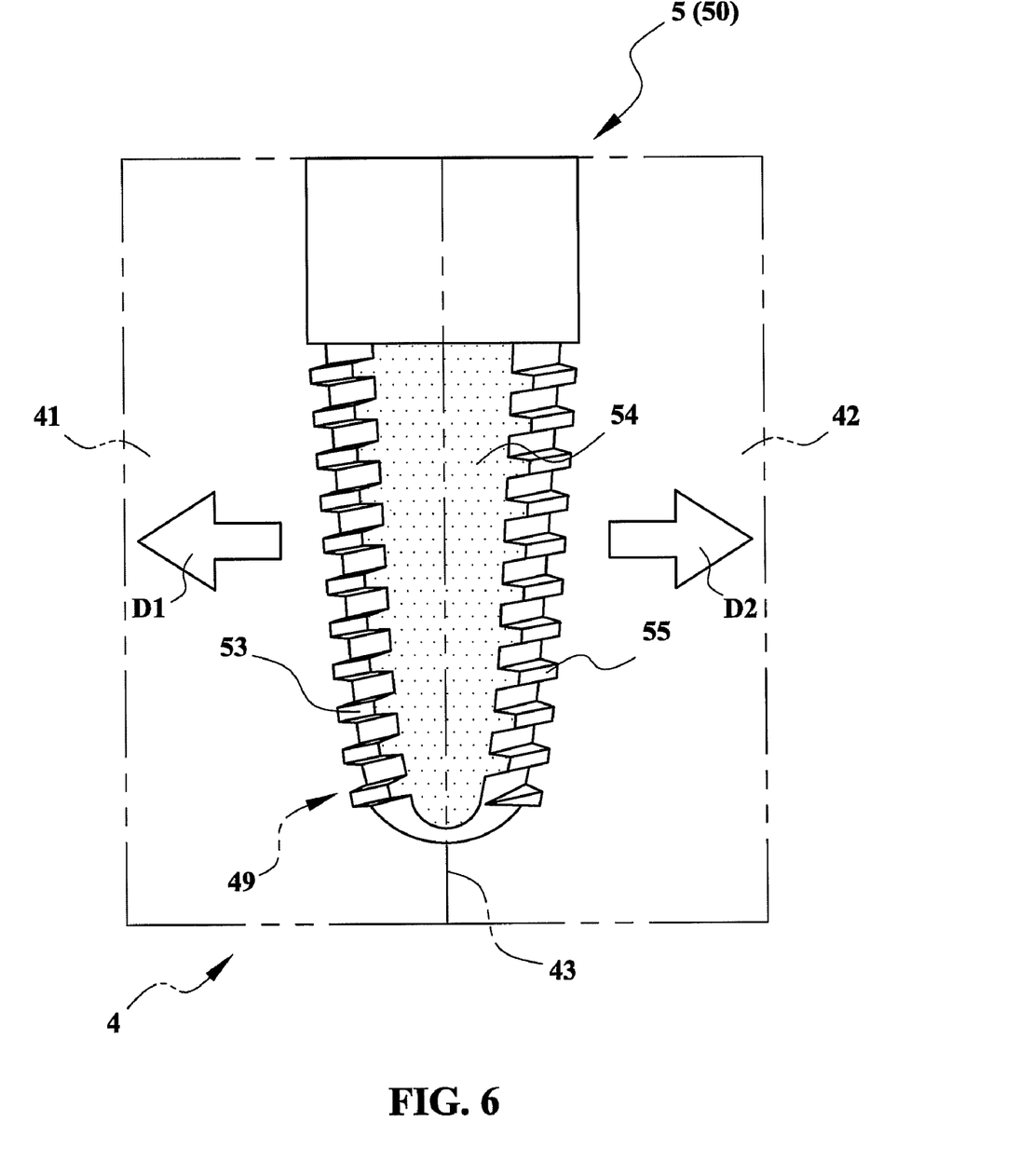
FIG. 6 is a schematic view showing a green body of the zirconium oxide dental implant having two non-thread sections and two external thread section formed by a mold cavity between two molding part according to the present invention.
Figure 7:
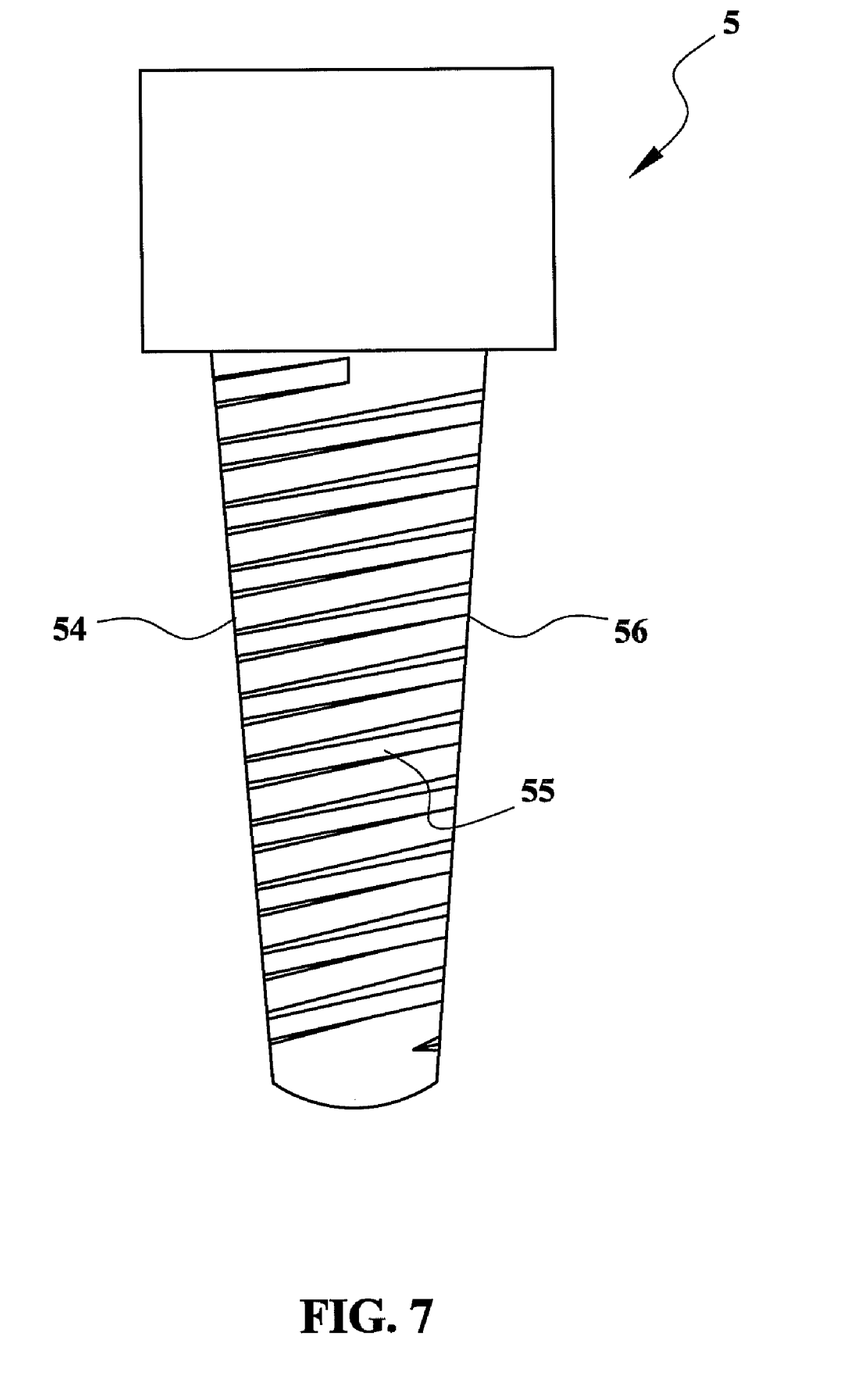
FIG. 7 is a schematic view showing a preferred embodiment of the zirconium oxide dental implant according to the present invention.

Referring to FIGS. 6 to 7, a preferred embodiment of the zirconium oxide dental implant 5 according to the present invention is obtained by injecting a zirconium oxide paste in a mold cavity 49 for forming a green body 50, and sintering the green body 50 in high temperature. The mold cavity 49 can be opened from the interface 43 in the opening directions D1 and D2 so as to discharge the green body 50.

The green body 50 of the zirconium oxide dental implant 5 is formed integrally with a first external thread section 53, a first none-thread section 54, a second external thread section 55, a second none-thread section 56. The first, external thread section 53 and the second external thread section 55 are formed on the peripheral of the green body 50 and divided by the first none-thread section 54 and the second none-thread section 56. In other words, the first none-thread section 54 and the second none-thread section 56 are formed on the opposite sides of the peripheral of the green body 50 and separated the first external thread section 53 and the second external thread section 55.

Figure 8:
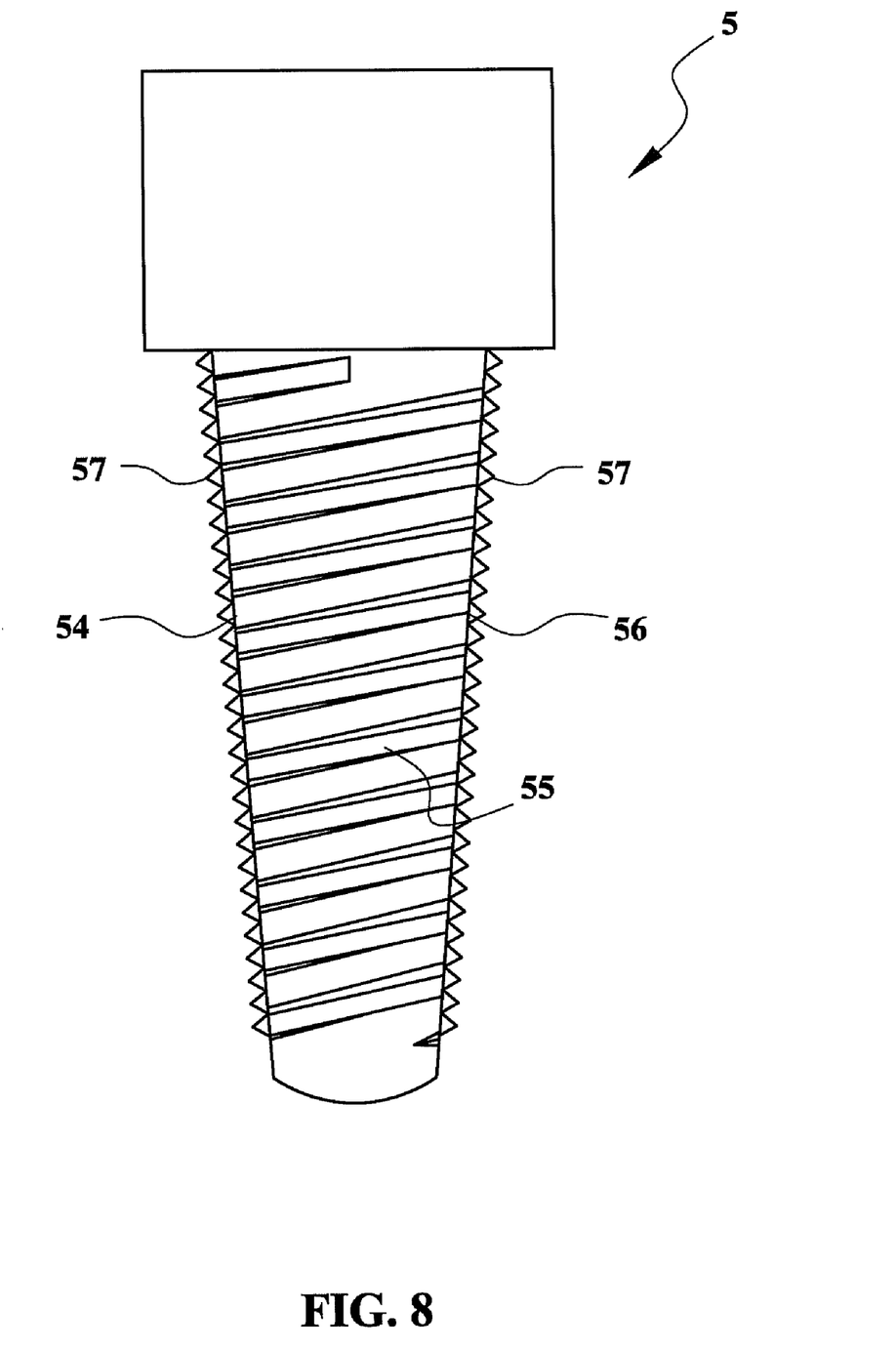
FIG. 8 is a side view showing an alternative embodiment of the zirconium oxide dental implant according to the present invention.
Figure 9:
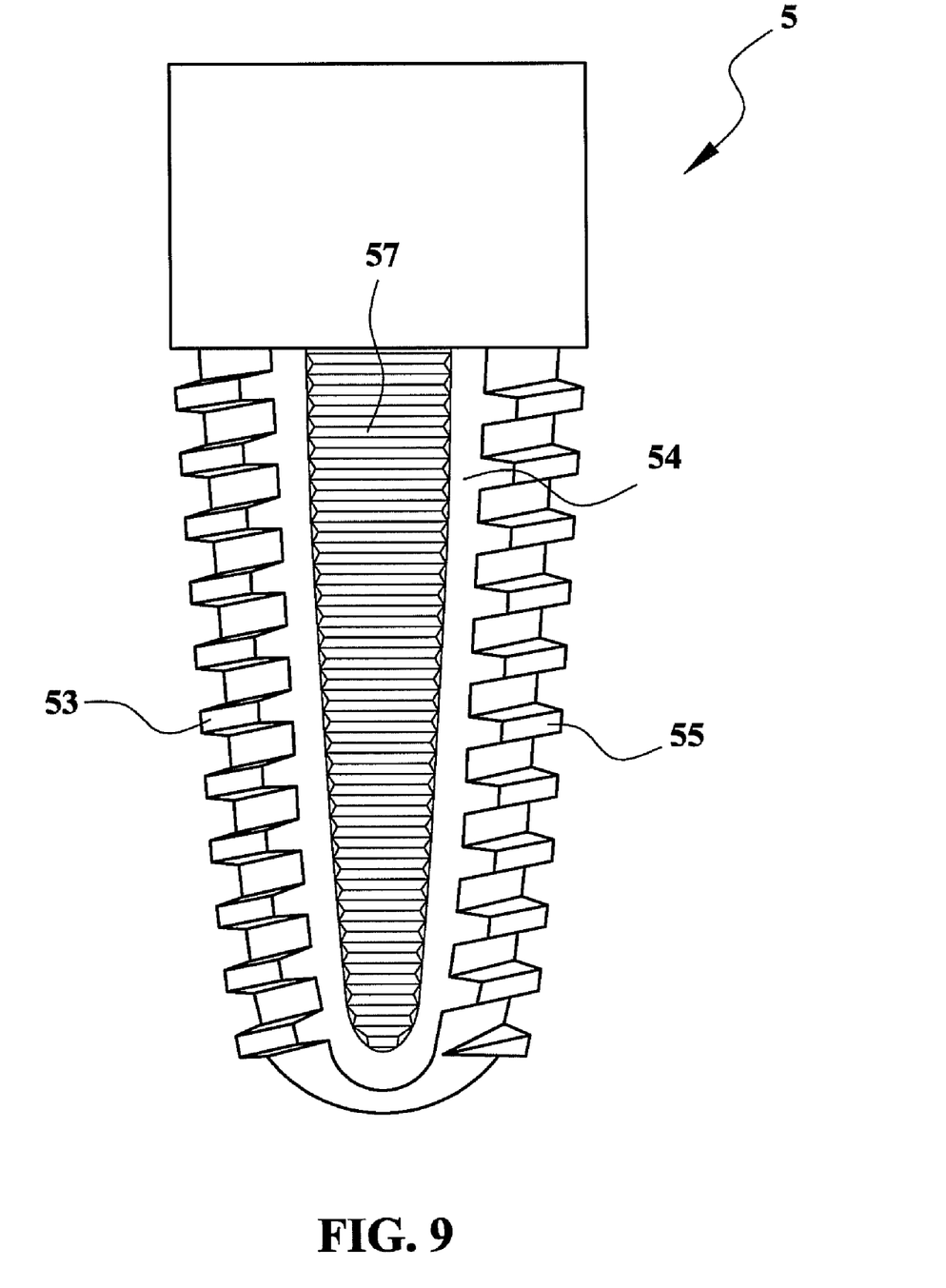
FIG. 9 is a front view showing the alternative embodiment of the zirconium oxide dental implant according to the present invention.

Referring to FIGS. 8 and 9, for enhancing the effect of the osseointegration for the zirconium oxide dental implant 5 in the alveolar bone 2, the first none-thread section 54 and the second none-thread section 56 of the green body 50 is preferably formed with a plurality of parallel grooves 57 or ribs paralleled to the opening directions D1 and D2, that can bite or cut into the cancellous portion of the alveolar bone 2. As the parallel grooves 57 or ribs are all paralleled to the opening directions D1 and D2, they shall not be distorted by the opening of the mold cavity 49.

Figure 10:
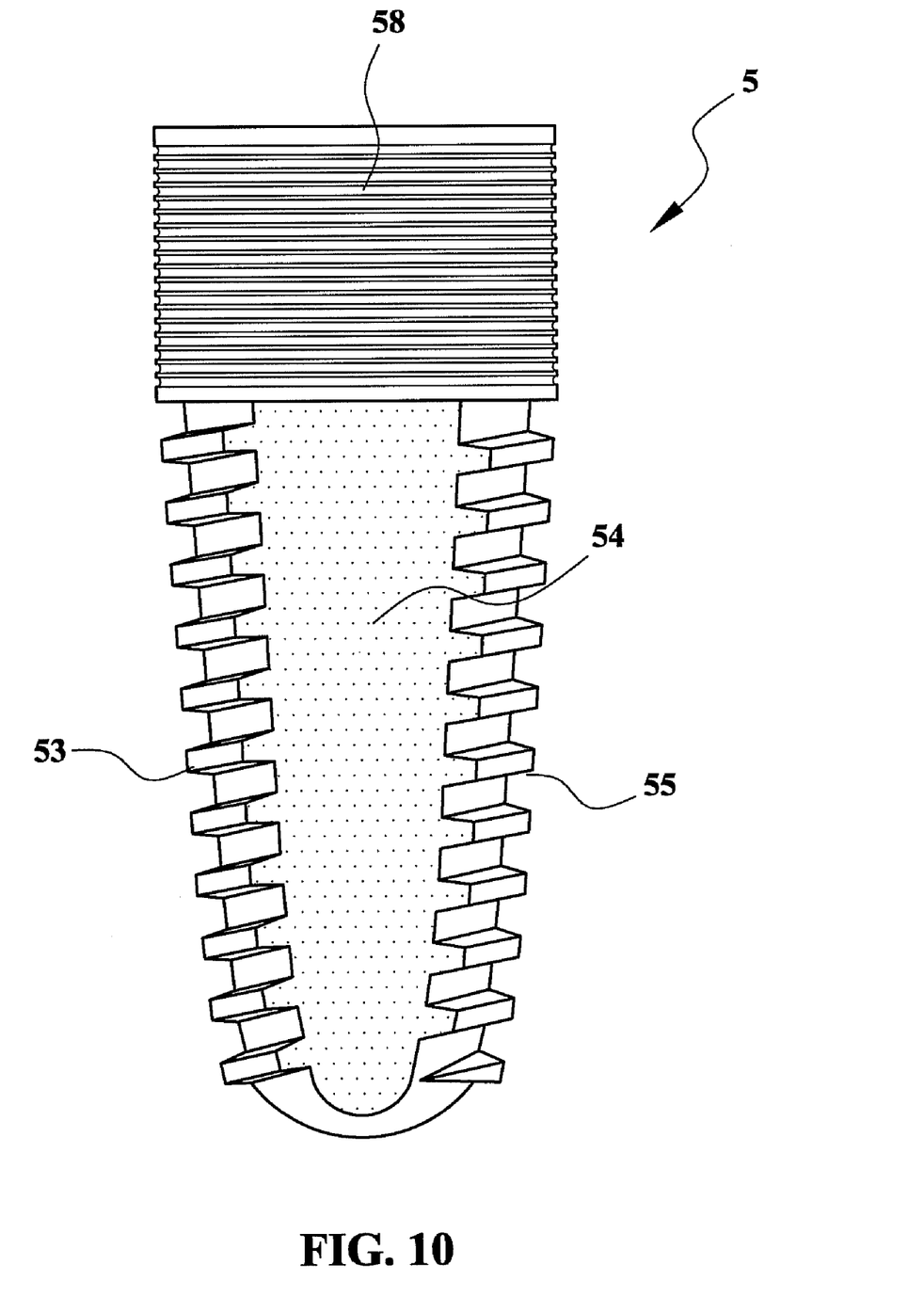
FIG. 10 is a front view showing another alternative embodiment of the zirconium oxide dental implant according to the present invention.

Referring to FIG. 10, in order to enhance the effect of the osseointegration for the zirconium oxide dental implant 5 in the alveolar bone 2, the green body 50 may be molded with an upper section 58 with a plurality of parallel grooves or ribs paralleled to the opening directions D1 and D2, that can bite or cut into the cortical portion of the alveolar bone 2. As the parallel grooves or ribs are formed on the upper section 58 paralleled to the opening directions D1 and D2, they shall not be distorted by the opening of the mold cavity 49.

Figure 3:
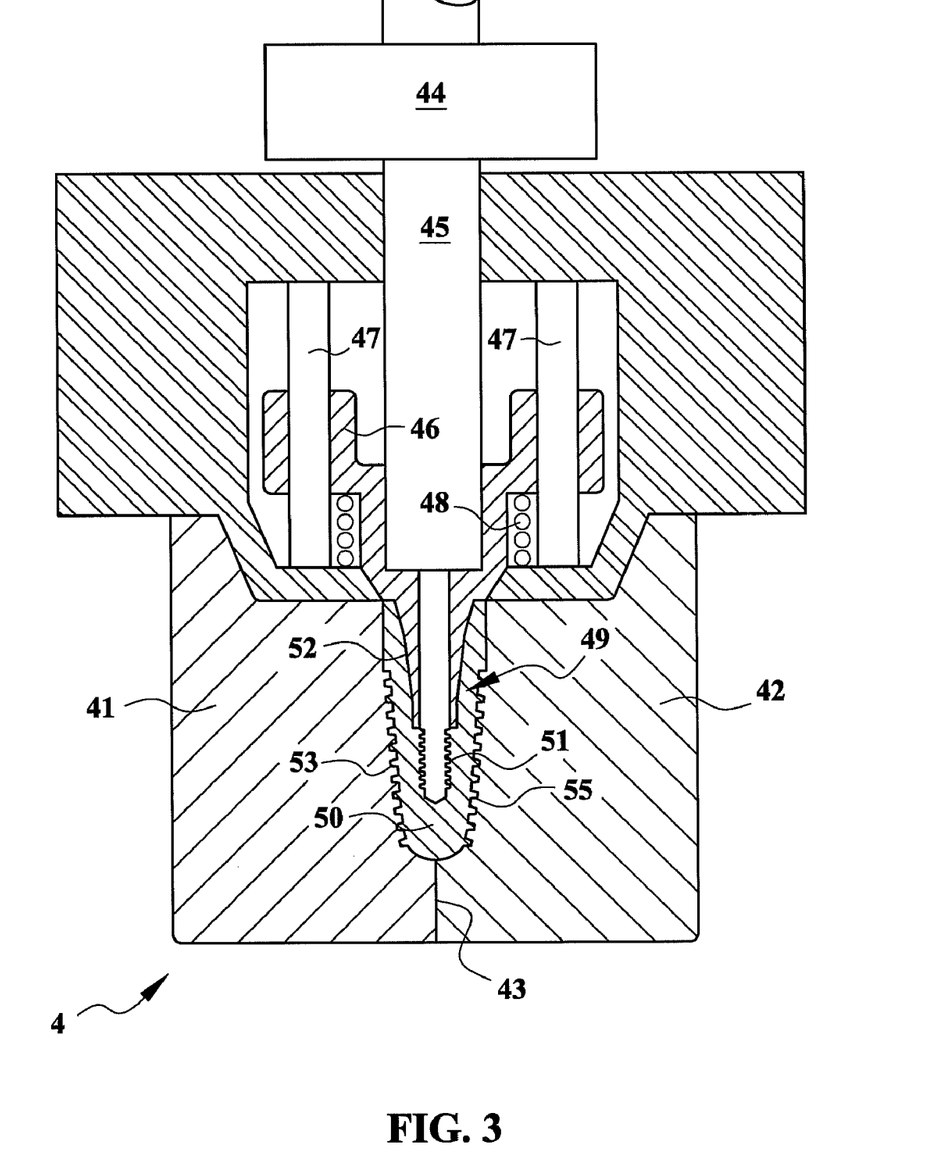
FIG. 3 is a cross-sectional schematic view illustrating a preferred embodiment of mold for molding a green body from zirconium paste according to the present invention; the green body can be sintered to be a zirconium oxide dental implant with remove any metal inserts from the green body.
Figure 4:
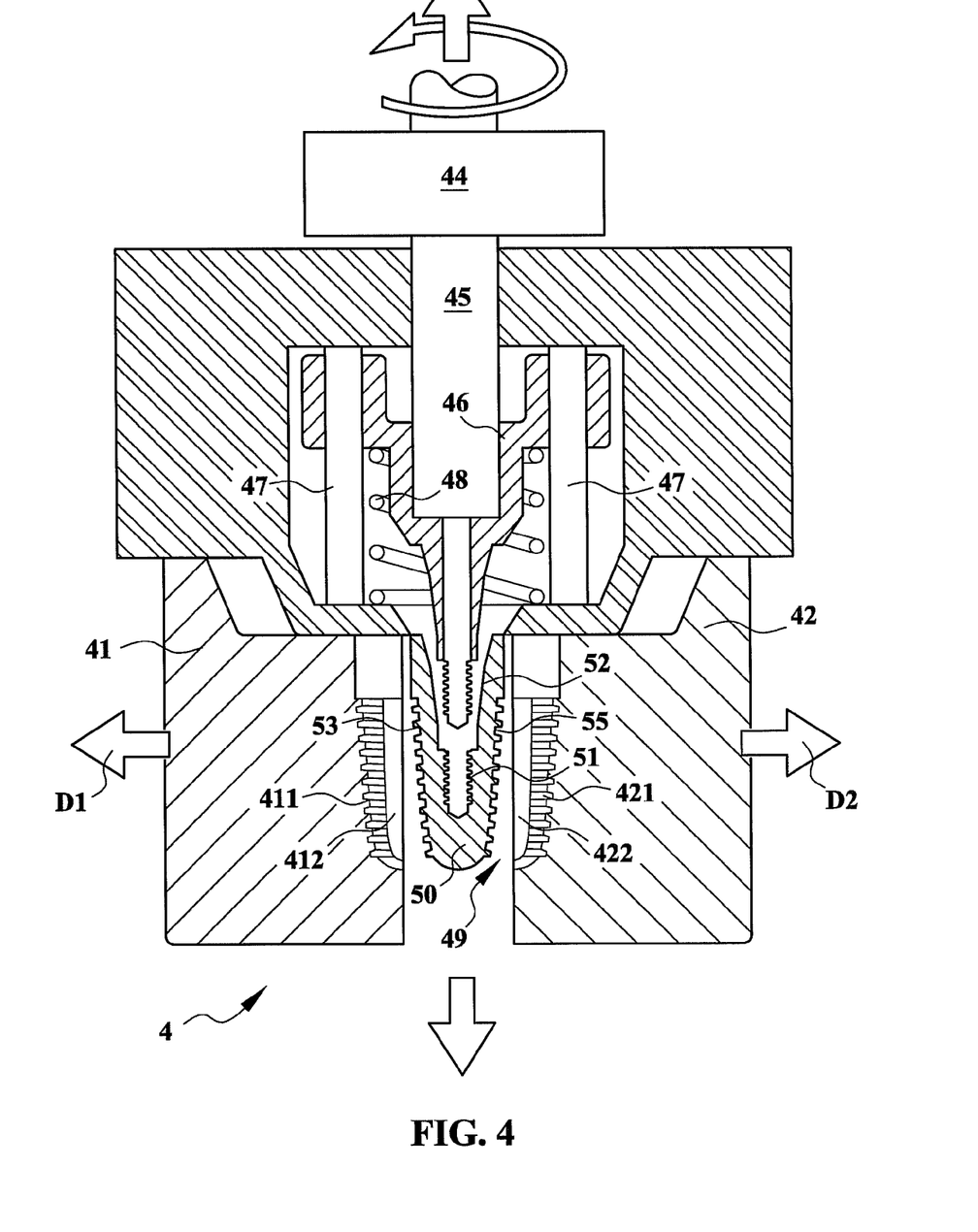
FIG. 4 is a cross-sectional schematic view illustrating the operation of molding a green body by the mold according to the present invention.

Referring to the preferred embodiment shown in FIG. 6, as well as the mold structure detailed in FIGS. 3 to 4, the mold 4 may include at least a first molding part 41 and a second molding part 42.

The first molding part 41 has a first imprinting inner surface 411 for forming the first external thread section 53, and two none-thread inner surfaces 412 for forming a half portion of the first none-thread section 54 and the second none-thread section 56 respectively.

The second molding part 42 has a second imprinting inner surface 421 for forming the second external thread section 56, and two none-thread inner surfaces 422 for forming a half portion of the first none-thread section 54 and the second none-thread section 56 respectively.

The first molding part 41 and the second molding part 42 have an interface 43 for closing with each other and forming a mold cavity 49. The none-thread inner surfaces 412, 422 are matched edge-to-edge on the interface 43 thereby forming the first none-thread section 54 and the second none-thread section 56 when the zirconium oxide paste is injected in the mold cavity 49.

Referring to FIGS. 3 and 4, the mold 4 may further include a driving mechanism 44, a polygonal conical slider 46, a screw thread forming rod 45 and a resilient element 48 for forming an internal thread 51 and polygonal tapering section 52 in the green body 50.

The driving mechanism 44 may include a motor and a ball screw (not shown) which drives the screw thread forming rod 45 to move in a pitch in every rotation.

Figure 5:
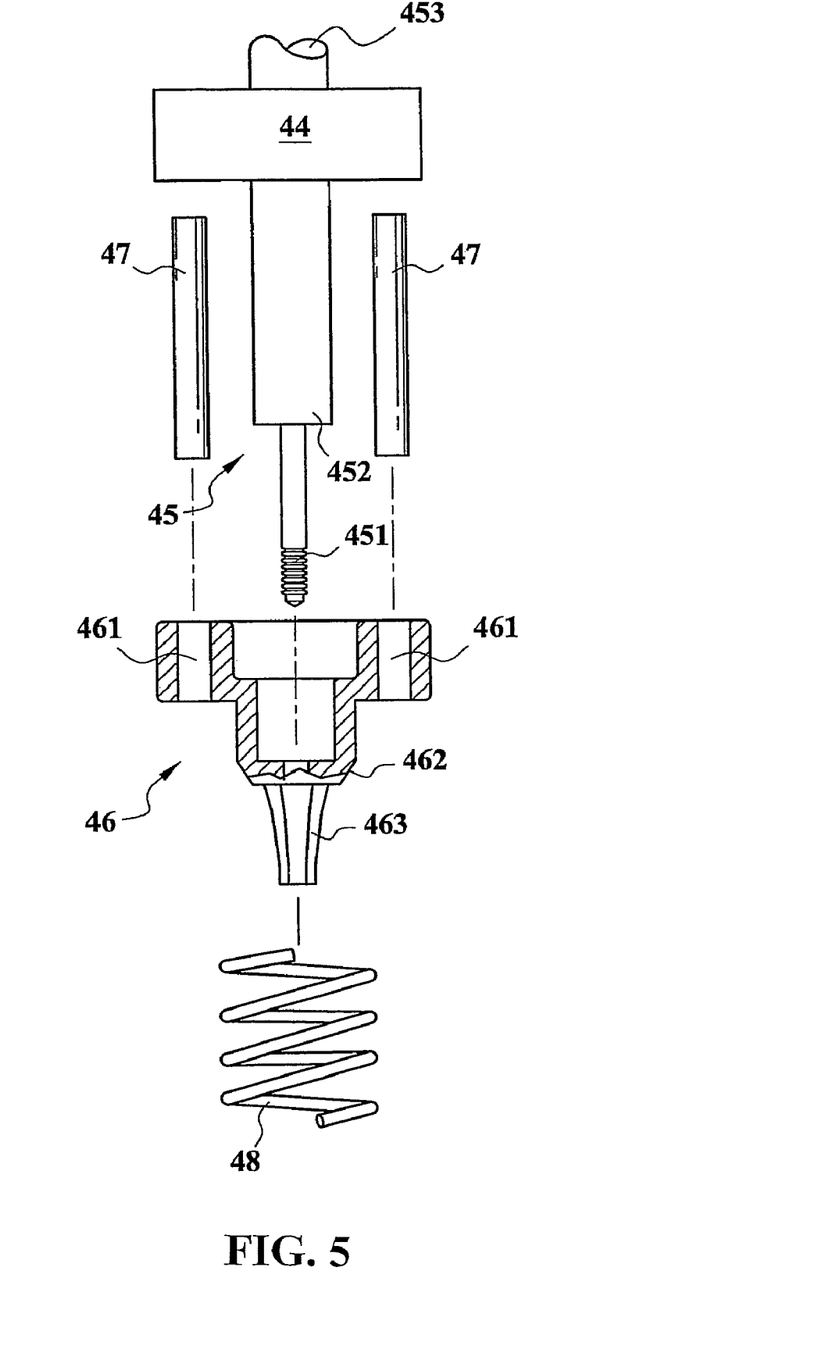
FIG. 5 is a cross-sectional exploded view illustrating a driving mechanism, screw thread forming rod and the polygonal conical slider of the mold according to the present invention.

Referring to FIG. 5, the screw thread forming rod 45 has a screw head portion 451 coaxially penetrated the polygonal conical slider 46 for forming the internal thread 51 of the green body 50, a shoulder portion 452 for abutting and pushing polygonal conical slider 46 toward the mold cavity 49, and one end 453 driven by the driving mechanism 44 to move axially a pitch in every rotation.

The polygonal conical slider 46 is pushed by the screw thread forming rod 45 toward the mold cavity 49 for forming a polygonal tapering section 52 of the green body 50, and biased by a resilient element 48 to leave the mold cavity 49 without performing rotation.

Preferably, the polygonal conical slider 46 may be formed with a positioning conical surface 462 for centering the screw thread forming rod 45 and the polygonal conical slider 46 within the mold cavity 49.

To prevent the polygonal conical slider 46 from rotation, the polygonal conical slider 46 is preferably formed with at least a guiding hole 461 and guided by a guiding rail 47. The polygonal conical slider 46 is formed with a protruded polygonal tapering head 463 for forming the polygonal tapering section 52 of the green body 50.

While particular embodiments of the invention have been described, those skilled in the art will recognize that many modifications are possible that will achieve the same goals by substantially the same system, device or method, and where those systems, devices or methods still fall within the true spirit and scope of the invention disclosed.

What is claimed is:

1. A mold for molding a green body of a zirconium oxide dental implant 5, including at least:

a first molding part, having a first imprinting inner surface for forming a first external thread section of the green body, and two none-thread inner surfaces oppositely formed beside the first imprinting inner surface for forming a half portion of a first none-thread section and a second none-thread section of the green body respectively;

a second molding part, having a second imprinting inner surface for forming the second external thread section of the green body, and two none-thread inner surfaces oppositely formed beside the second imprinting inner surface for forming another half portion of the first none-thread section and the second none-thread section of the green body respectively;

a driving mechanism;

a polygonal conical slider may be pushed toward the mold cavity for forming a polygonal tapering section of the green body, and biased by a resilient element to leave the mold cavity without performing rotation; and a screw thread forming rod having a screw head portion coaxially penetrated the polygonal conical slider for forming a internal thread of the green body, a shoulder portion for abutting and pushing the polygonal conical slider toward the mold cavity, and one end driven by the driving mechanism to move axially a pitch in every rotation, wherein the first molding part and the second molding part have an interface for closing with each other and forming a mold cavity, and the none-thread inner surfaces are matched edge-to-edge on the interface thereby forming the first none-thread section and the section and the second none-thread section of the green body when a zirconium oxide paste is injected in the mold cavity.

2. The mold according claim 1, wherein the polygonal conical slider has a positioning conical surface for centering the screw thread forming rod and the polygonal conical slider 46 within the mold cavity.

3. The mold according to claim 1 wherein the polygonal conical slider is formed with a protruded polygonal tapering head for forming the polygonal tapering section of the green body.

4. The mold according to claim 1, wherein the polygonal conical slider is formed with at least a guiding hole and guided by a guiding rail.

* * * * *